United States Patent [19]

Delk et al.

[11] Patent Number: 5,292,312
[45] Date of Patent: Mar. 8, 1994

[54] UNIVERSAL TUBE LUMEN CATHETER HOLDER

[75] Inventors: Robert E. Delk; Sharon D. Cheatwood, both of Dallas; Michael L. Bowen, Arlington, all of Tex.

[73] Assignee: Struckmeyer Corporation, Dallas, Tex.

[21] Appl. No.: 2,313

[22] Filed: Jan. 8, 1993

[51] Int. Cl.⁵ .............................................. A61M 25/02
[52] U.S. Cl. ............................ 604/180; 128/DIG. 26
[58] Field of Search ...................... 604/174, 179, 180; 128/DIG. 26, DIG. 6

[56] References Cited

U.S. PATENT DOCUMENTS

| | | | |
|---|---|---|---|
| 3,288,136 | 11/1966 | Lund | 128/DIG. 26 |
| 3,677,250 | 7/1972 | Thomas . | |
| 3,726,280 | 4/1973 | Lacount . | |
| 3,765,421 | 10/1973 | Poprick . | |
| 3,826,254 | 7/1974 | Mellor | 604/180 |
| 3,834,380 | 9/1974 | Boyd | 604/180 |
| 3,878,849 | 4/1975 | Muller et al. | 128/DIG. 26 |
| 4,096,863 | 6/1978 | Kaplan et al. | 604/179 |
| 4,165,784 | 8/1979 | Johnson . | |
| 4,333,468 | 6/1982 | Geist . | |
| 4,445,894 | 5/1984 | Kovacs | 604/179 |
| 4,571,245 | 2/1986 | Hubbard et al. | 128/DIG. 26 |
| 4,583,976 | 4/1986 | Ferguson . | |
| 4,617,017 | 10/1986 | Hubbard et al. | 128/DIG. 26 |
| 4,702,736 | 10/1987 | Kalt et al. . | |
| 4,726,716 | 2/1988 | McGuire . | |
| 4,738,662 | 4/1988 | Kolt et al. | 128/DIG. 26 |
| 4,976,700 | 12/1990 | Tollini | 128/DIG. 26 |
| 4,988,338 | 1/1991 | Taylor | 604/180 |
| 5,037,397 | 9/1991 | Kolt et al. | 604/179 |
| 5,147,322 | 9/1992 | Bowen et al. | 604/180 |

OTHER PUBLICATIONS

Utah Medical Brochure, page showing tube holder of APLIX, Inc., circa 1990.

*Primary Examiner*—Paul J. Hirsch
*Attorney, Agent, or Firm*—Richard C. Litman

[57] ABSTRACT

A medical conduit holder for securing medical conduits to the skin of a patient is made of two major portions. The first portion is a base plate or patch for adhesively securing to the skin. The second portion is a strap which wraps back through a slot in the strap to fully encircle the conduit or group of conduits. Pressure sensitive VELCRO type attachment surfaces are present on the upper surface of the base plate and the lower surface of the strap. The externally exposed parts of both the base patch and the strap are smooth so as not to snag on surrounding materials. The surface of the strap which contacts the conduit is made of or coated with a high friction material to prevent axial slipping of the encircled conduit. Typical conduits which may be conveniently held in place with this invention include tubes, lumens, catheters, electrical wiring, and optical fibers. The conduits may easily be oriented in any direction and may be removed or replaced without the necessity of removing the adhesive from the patient.

15 Claims, 3 Drawing Sheets

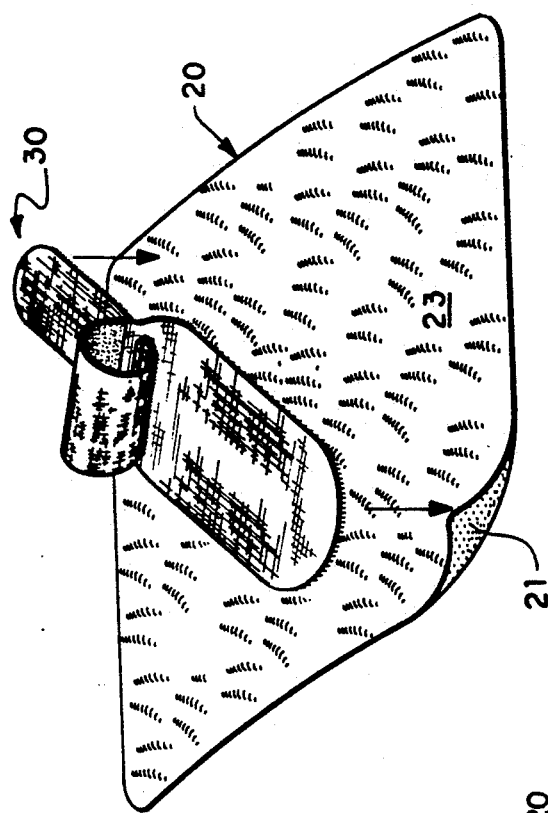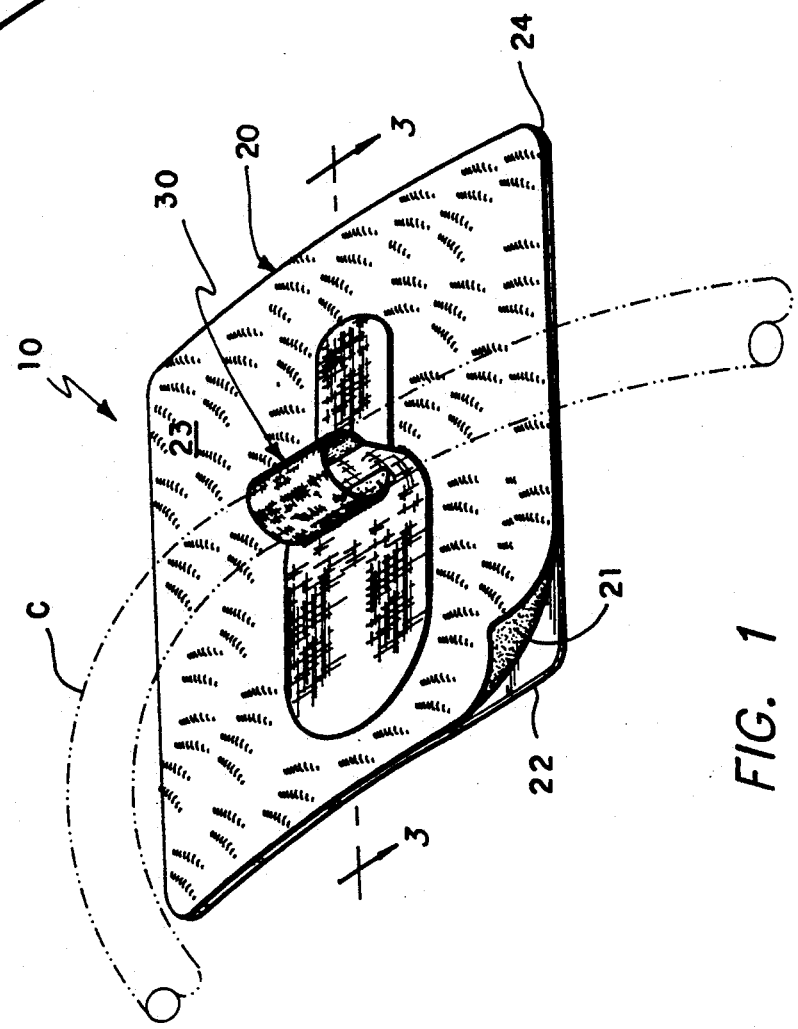

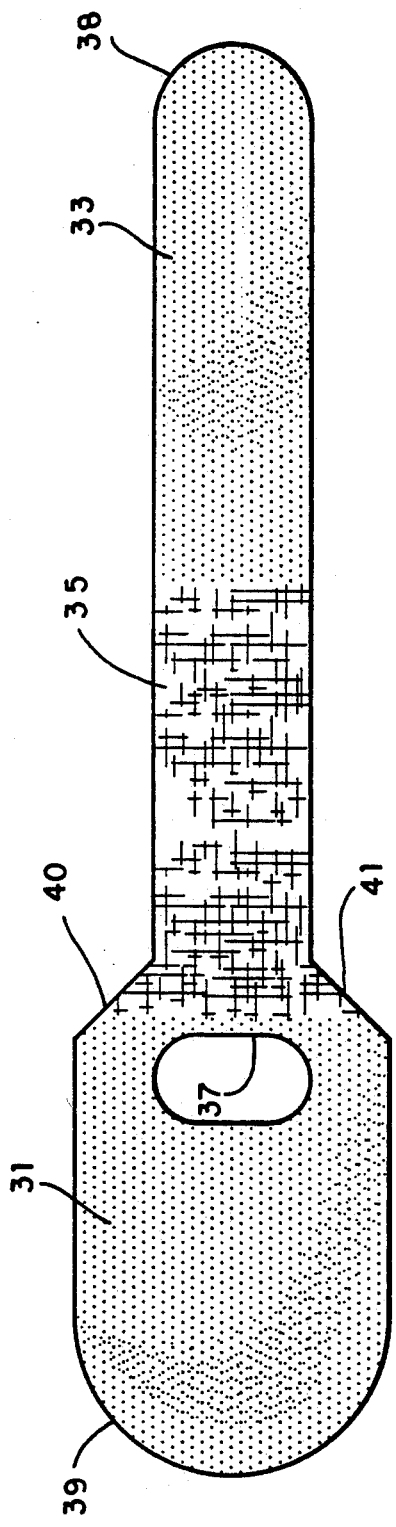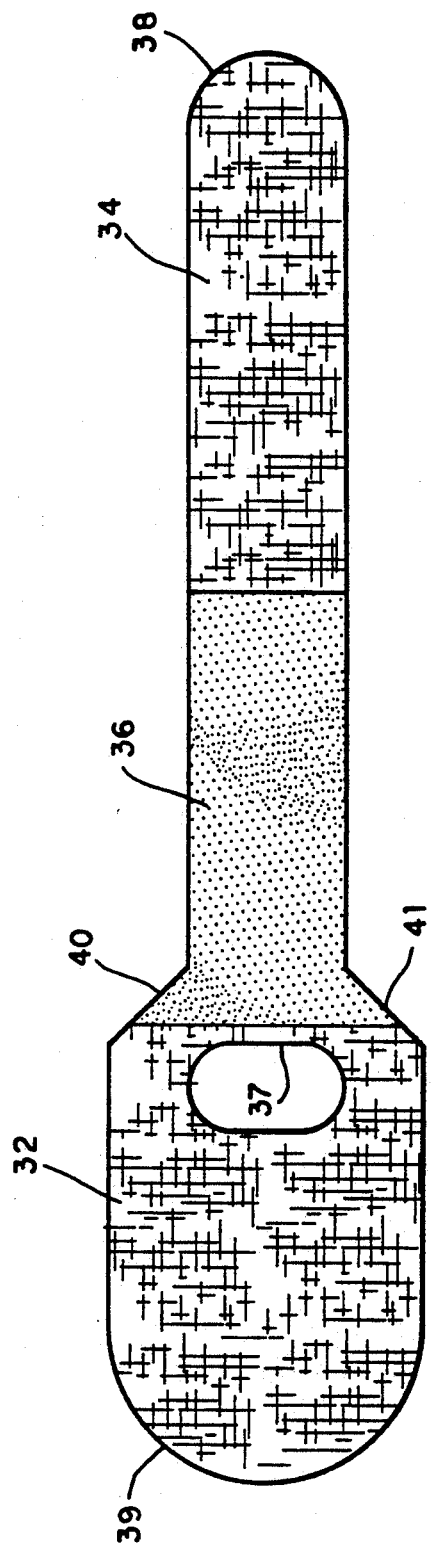

UNIVERSAL TUBE LUMEN CATHETER HOLDER

BACKGROUND OF THE INVENTION

1. Field of the Invention

The present invention relates generally to a clamp for adjustably holding an article to the surface of an object and more particularly to a clamp capable of holding medical conduits to a patient's body in conjunction with numerous medical treatments and procedures. In the broad sense this invention is useful for firmly holding any long slender conduit of indefinite length, such as a tube, pipe, optical fiber, or electrical wire, to a surface in an infinitely adjustable orientation. A myriad of medical treatments and procedures require external and mesentery conduits and thereby require apparatus for releasably holding the conduits in place in a convenient and inexpensive manner. As a result the invention applied to numerous and diverse specialties within the medical field. For example, lumen injection cannulae, feeding tubes, nasogastric tubes, foley catheter and condom catheter tubes, dialysis tubes, angiocath and heparin lock set tubes, luer locks as well as other tubes used to introduce liquids into the body intravenously or to introduce oxygen into the mouth or nose of the patient may be adequately supported by means of this invention. Electrical wiring and other patient monitoring type conduits may also be conveniently held in place so as to prevent entanglement or dislodging during patient movement.

2. Description of the Prior Art

There has long been a need for a simple but universal tube, lumen, and conduit (TLC) holder for bedridden patients. For years the best devices available for releasably but firmly retaining conduits upon a patient were dependent upon adhesive tape attached directly to the skin. Rarely do medical personnel have the skill to make a proper mesentery support using ordinary hospital self adhesive tape for holding a catheter or tube to the skin. When the personnel have sufficient skill, such ordinary tape does not work well because it is too pliable and pulls off the skin too easily. Tape has proven unsatisfactory because it must be removed each time the held item is changed, causing discomfort to the patient and possible skin damage. Moreover, the items are usually not held sufficiently securely, and are likely to move relative to the patient each time the patient moves, again causing pain and possible injury or even complete dislodging of the item. Conduits of this nature often need to be reoriented or replaced requiring frequent irritating pulling of adhesive tape support structure from the sensitive epidermal layer of the patient. Various devices for holding either an injection cannula or an infusion tube in place have been developed heretofore. Most prior conduit holders have made it difficult or impossible to realign the conduits in a different direction without the complete removal of the conduit. Prior conduit holders have also been difficult or impossible to trim to size for fitting to the patient. Prior holders suffer from an inability to firmly hold conduits in their lengthwise direction. In other words it was easy for the captured conduit to slide longitudinally with respect to the holder. Another common problem with prior conduit holders is that they tend to get caught in bed linen and clothing due to bulkiness or exposed tacky surfaces.

U.S. Pat. No. 4,571,245 issued to Hubbard et al on Feb. 18, 1986 shows a personal catheter leg strap which appears, at least superficially, like the instant invention in that they both employ VELCRO fastened straps encircling a catheter tube. However, in direct contradistinction the instant invention, Hubbard's holder must be wrapped around a limb of the patient thus limiting its use to the area of the limbs. Hubbard's holder cannot be adjustably oriented in direction. Hubbard's strap must be wrapped an additional half turn about the tubing so as to prevent the artificial burr material from exterior exposure. However, this direction of wrapping makes the support weaker by requiring the VELCRO attachment points to be located some distance from the supported tube. Hubbard does not address the problem of axial slippage of the supported tube in this patent.

U.S. Pat. No. 4,617,017 issued to Hubbard et al on Oct. 14, 1986 is a continuation-in-part of the above mentioned U.S. Pat. No. 4,571,245. This patent specifically addresses the axial slippage problem. The burr type appendages of VELCRO material are wrapped so as to hopefully dig into the soft outer surface of a wrapped tube. Of course if the tubing or conduit has a hard surface this strategy will fail. In contradistinction, the instant invention utilizes a high friction material to provide a more general and positive gripping of a wrapped tube regardless of the firmness of its exterior and the wrapping direct.

U.S. Pat. No. 4,702,736 issued to Kalt et al on Oct. 27, 1987 shows a tubing clamp utilizing a strap having VELCRO fastening means for holding the tubing down against a resilient base. Kalt's holder is not directionally adjustable nor does it completely encircle the tubing. In contradistinction, the instant invention completely encircles the tube and it is infinitely adjustable.

U.S. Pat. No. 4,583,976 issued to Ferguson on Apr. 22, 1986 shows catheter support adhesively attached to the skin. The support is not directionally adjustable nor does it completely encircle the tubing. In contradistinction, the instant invention completely encircles the tube and is infinitely adjustable.

U.S. Pat. No. 4,333,468 issued to Geist on Jun. 8, 1982 shows a mesentery tube holder apparatus which adhesively attaches a tube to a patient's body. Geist's support is not directionally adjustable nor does it completely encircle the tubing. In contradistinction, the instant invention completely encircles the tube and is infinitely adjustable in direction.

U.S. Pat. No. 3,834,380 issued to Boyd on Sep. 10, 1974 shows a holder for intravenous injection cannula and tubing. Boyd uses a separate clamping tube for supporting the catheter tube which is in turn held shut by a VELCRO strip. This holder is not adaptable to different sized tubing nor is it directionally adjustable. In contradistinction, the instant invention will hold conduits of all sizes is infinitely adjustable in direction.

U.S. Pat. No. 4,165,784 issued to Johnson on Aug. 28, 1979 shows a catheter tube holder forming a double bridge member supporting the tube. The tube support does not grasp the tube securely. Thus, the tube can slide back and forth through the tube holder. Further, if it is desired to reorient the direction of the tube, the entire Johnson patch and holder must be lifted, adhesive and all, and reattached to the patient's skin. In direct contradistinction, the instant invention holder grasps the tube securely and may be reoriented to change the direction of the tube without disturbing the base patch at all. Also, its range of directional adjustment is infinite. Also, the Johnson holder, since it reattaches to itself, locates the tube well above the base and the patient's skin, where it can catch on bed linens, and is prone to flopping back and forth; both are undesirable features of this holder. On the other hand, the instant invention provides a low profile tube holder which also secures the holder firmly and directly against the patch and thus the patient U.S. Pat. No. 4,726,716 issued to McGuire on Feb. 23, 1988 shows a fastener for a Foley catheter having an opening for inserting a second passage of the catheter. McGuire's support is adhesively attached directly to the skin and is not directionally adjustable. In contradistinction, the instant invention is not directly adhered to the skin and its directional adjustment range is infinite.

U.S. Pat. No. 3,677,250 issued to Thomas on Jul. 18, 1972 shows a tabbed anchoring tape means for anchoring medical tubing. Thomas's tape is adhered to the skin of the patient and wrapped around the tubing but in no other way resembles the instant invention.

U.S. Pat. No. 3,878,849 issued to Muller et al on Apr. 22, 1975, U.S. Pat. No. 3,765,421 issued to Poprick on Oct. 16, 1973, and U.S. Pat. No. 3,726,280 issued to Lacount on Apr. 10, 1973 show catheter or surgical tube supports which are designed to encircle a limb of the patient. In contradistinction, the instant invention does not require the encircling of a limb to establish a firm support base.

U.S. Pat. No. 3,288,136 issued to Lund on Nov. 29, 1966 shows a tube lock for releasably anchoring a medical tube to the skin of a patient. Lund uses VELCRO fastening means and an auxiliary tube to secure the tubing against lengthwise movement. The auxiliary tube causes the Lund device to be useful only for tubing of a certain diameter. In contradistinction, the instant invention may securely hold tubes or bundles of tubes of any diameter.

The brochure of Utah Medical of Midvale, Utah, circa 1990, shows a tube holder of Aplix, Inc. This Aplix holder has a plain back surface and hook material on the opposite surface, and includes a wide base end, a narrow end tab, and an aperture through the base end adjacent the narrow tab. The tab, however, is wrapped about the tube, forwardly from the base end, then inserted back through the aperture, and wrapped again, over the tab portion on top of the tube, and placed down on a loop material base. While a smooth, upper (back) surface is thus presented to the environment, the wrap of an extra one half time about the tube spreads the hooks of the holder wide apart from the tube. Thus, an insecure attachment is made to the narrow length loop material adhesive patch or limb wrap, shown in the Aplix, Inc. disclosure. In direct contradistinction thereto, the present invention is structured so that an almost unbroken surface of hook material is placed down on the loop material base, the tab end of the holder being inserted through the base end aperture of the holder, oppositely of the Aplix, Inc. disclosure, so that a much firmer securement is made, of the tube to the adhesive patch base and the patient. Further, a portion of otherwise exposed hook material on the holder above the tube is removed, so that a clean, non-snag surface is presented to the environment. Also, the instant invention provides high friction material adjacent the enclosed catheter tube to prevent any lengthwise movement, and, further, the holder of the instant invention is adjustable through a full circle with respect to an adhesive patch attached to the patient; neither of these features is in any way suggested by the Aplix, Inc. disclosure.

None of the above inventions and patents, taken either singly or in combination, is seen to describe the instant invention as claimed.

SUMMARY OF THE INVENTION

This invention provides a belt like wraparound medical conduit holder. The wrapping strap is mounted on a relatively large base portion which is adhesively attached to the skin of the patient one time only. A medical grade adhesive compatible for use on a living body is used. Subsequent changes of the holding strap such as for reorientation or tubing changes are made without removal of the adhesive from the patient. The large base portion is to permit an infinite range of directional adjustment. The strap portion of the holder is reusable and sterilizable. Attachment between the strap portion and the base portion is preferably accomplished by an artificial burr material such as VELCRO. The strap is wrapped in such a direction as to hold the conduit next to the skin with a minimal amount of play. The "hooks" of the VELCRO are on one side of the strap portion whereas the "loops" are on the side of the base portion opposite the adhesive. The portion of the strap adjacent the conduit in the wrapped condition is coated with a high friction material to reduce axial slippage. The portion of the strap opposite the conduit in the wrapped condition has the "hooks" of the VELCRO material burned off or otherwise removed so as not to accidentally grab upon foreign material.

Accordingly, it is a principal object of the invention to provide a medical conduit holder for holding a conduit on the body of a patient which is directionally adjustable so as to infinitely vary the orientation of the conduit with respect to the patient.

It is another object of the invention to provide a medical conduit holder that can be removed or reoriented without tearing any adhesive bonds from the skin of the patient.

It is a further object of the invention to provide a medical conduit holder which presents no external protuberances, corners, or edges to catch upon or otherwise bind with surrounding objects such as bed linens, other bandages, or clothing.

Still another object of the invention is to provide a medical conduit holder which is fully operational to hold one or a bundle of several conduits of virtually any type, shape, size, or firmness.

Still another object of the invention is to provide a medical conduit holder suitable for holding conduits fully capable of transmitting bodily fluids, electrical signals, or light waves.

Still another object of the invention is to provide a medical conduit holder which provides a strong positive support for the conduit by connecting the tubing to the patient's skin surface very near the portion of the conduit which is closest the skin surface.

Still another object of the invention is to provide a medical conduit holder which fully encircles the held conduit with a single unitary strap so as to provide maximum holding power.

Still another object of the invention is to provide a medical conduit holder which includes a high friction coating on the portion adjacent the conduit so as to provide maximum gripping power and in particular to prevent slippage of the conduit in its axial direction.

Still another object of the invention is to provide a medical conduit holder which distributes the total holding force over a relatively large area of the conduit to thus provide a large holding force with a relatively low pressure and consequent minimal constriction of the held conduit.

Still another object of the invention is to provide a medical conduit holder which is easily releasable from the conduit so that the tubing may be replaced without replacing or disturbing the original orientation of the holder.

Still another object of the invention is to provide a medical conduit holder which may be trimmed to conveniently fit upon virtually any area of a patient's skin surface be they infant or adult.

Finally, it is a general object of the invention to provide improved elements and arrangements thereof in an apparatus for the purposes described which is inexpensive, dependable and fully effective in accomplishing its intended purpose.

It is submitted that the present invention meets or exceeds all the above objects and goals. Upon further study of the specification, drawings, and appended claims these and other objects and advantages of the present invention will become readily apparent.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein:

FIG. 1 is a perspective view of the tube, lumen, and catheter (TLC) holder shown in an operative position holding a broken away piece of medical conduit shown in phantom lines.

FIG. 2 is a perspective view of the TLC holder lifted from and rotated with respect to its base portion.

FIG. 5 is a top view of the strap portion of the TLC holder as it appears when unwrapped and laid flat.

FIG. 6 is a bottom view of the strap shown in FIG. 5.

Similar reference characters denote corresponding features consistently throughout the attached drawings.

DETAILED DESCRIPTION OF THE PREFERRED EMBODIMENT

Figure 3:
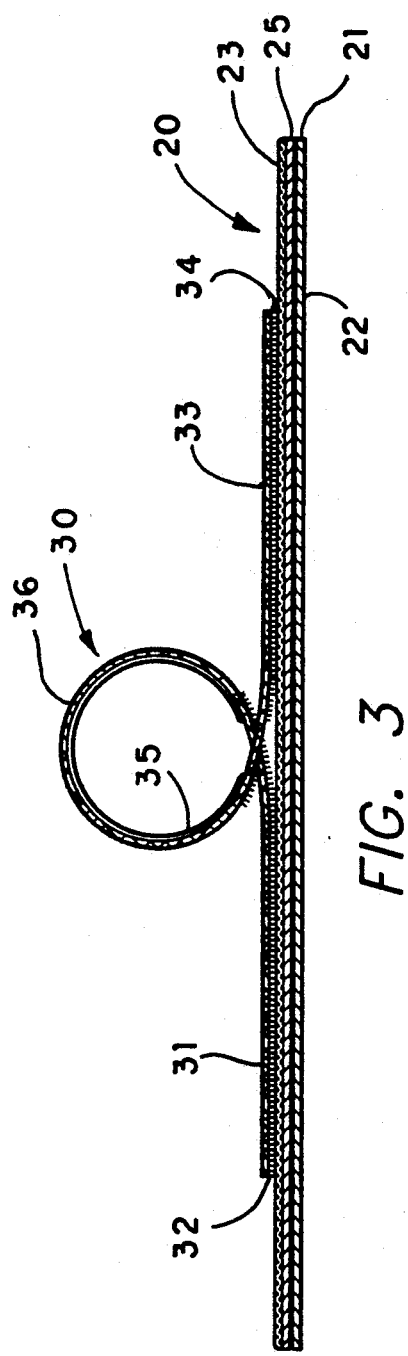
FIG. 3 is a sectional view of the TLC holder taken along line 3—3 of FIG. 1.

Referring now to FIG. 1, tube, lumen and catheter (TLC) holder 10 is shown holding a typical portion of medical conduit C. It should be understood from the outset that medical conduit C, shown in phantom, could represent fluid tubing, electronic wiring, or fiber optic strands, or any other elongated object used in conjunction with modern medical procedures. The material from which holder 10 is constructed is mechanically strong and light, electrically insulative and non-inductive, magnetically permeable, thermally non-conductive, and chemically inert. It is contemplated that an entire bundle comprising many different sizes and types of medical conduits could be wrapped as a unit and supported by the holder of this invention. The phrase "medical conduit" is meant to include tubing of all sizes and types both rigid and flexible for transporting fluids to and from the body, electrical wiring for transmitting electrical signals to or monitoring signals from the body, and optic fibers for similar transmission of light signals.

The TLC holder 10 comprises base plate 20 and strap portion 30. Base plate 20 is formed of a moderately pliable material that will contour to a patient's skin and still be easy to trim to size for special applications such as for use with infants. The lower portion of the base plate 20 is covered with a medical grade self adhesive coating 21 compatible for use on a living body. Substrate film 22 covers the adhesive 21 for shipping and handling and is designed to be peeled away and discarded at the use site in the conventional manner. A hypoallergenic synthetic acrylic pressure sensitive adhesive may be used. More specifically, a homogeneous blend of one or more water soluble and/or water swellable hydrocolloid dispersed in a viscous elastomeric substance such as polyisobutylene may be used as is well known in the adhesive art. Alternately, the adhesive composition can also include one or more cohesive strengthening agents or one or more hydratable natural or synthetic polymers. Since it is contemplated the base plate may be left upon the patient for relatively long periods of time (through several changes of strap portion 10 and its associated conduits) it is particularly important that the adhesive chosen be non irritating to the skin. Preferably, it should also be semi-porous or air permeable so as not to completely seal the skin from at least limited contact with the atmosphere.

Base plate 10 is illustrated as being substantially square with rounded corners. This configuration is preferable as a starting shape for the base because it allows strap portion 30 to be placed upon the base plate at any angle throughout a full 360 degree range. Of course, when the strap angle is changed the attendant direction of the supported tube is also changed with respect to the body of the patient. This invention is particularly adaptable to precise and fine adjustment of the mounting angle. The placement of the strap portion 30 upon base plate 20 is more fully described hereinafter. Corners of the square base plate are rounded as shown at 24 to reduce stress concentrations and thus prevent inadvertent peeling of the base from the patient. It is to be understood that the base plate may be easily trimmed to fit as needed for application to any special area of the skin such as the facial area. It will also be understood that the overall size of the base plate 20 and its detachable strap portion 30 may be varied over a wide range with the only requirement being that the base plate be large enough to accommodate the strap portion. To facilitate the desired air permeability base plate 20 may be perforated with a multitude of micro pores or small holes if desired.

The upper surface 23 of base plate 20 is covered with loop type VELCRO material so as to present a smooth exposed surface while serving as a convenient and large attaching point for the hook type VELCRO material of strap portion 30. The large upper surface area allows the initial positioning of the TLC holder over a wide range of lateral distances and angles. For example, FIG. 2 shows strap portion 30 as it would appear after lifting it from the position of FIG. 1 and rotating it about 45 degrees. The two downward arrows in FIG. 2 indicate the next motion which is to lower strap portion 30 so as to reattach it to base plate 20. The net effect is thus to reorient the direction of medical conduit C without disturbing either end of the conduit or peeling any adhesive from the patient. It will be obvious that a certain amount of lateral adjustment of the conduit could be similarly achieved.

Figure 4:
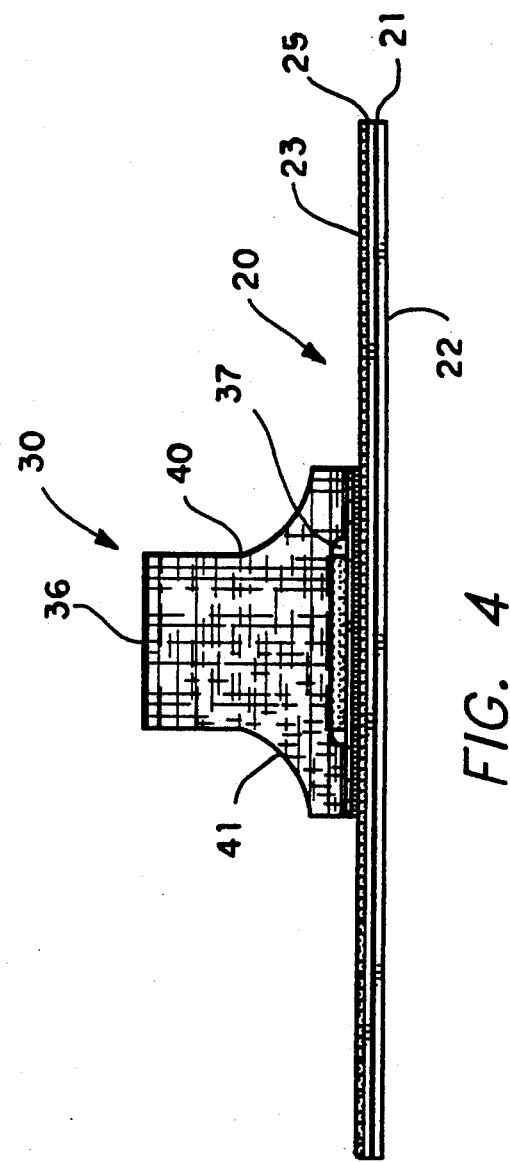
FIG. 4 is a side view of the TLC holder as seen from the right side of FIG. 1.

FIGS. 5 and 6 show the strap portion 30 when unwound and laid flat as it would be prior to use with FIG. 5 showing the top or side and FIG. 6 showing the bottom. Strap 30 is generally a long thin strip being wider at the left end than the right end as seen in FIGS. 5 and 6. A rounded slot 37 is formed in the strap near the transition zones 40, 41 between the wide and narrow portions of the strap. The wide end is rounded as at 39 and the narrow end is rounded as at 38. Both the top and bottom sides of the strap have their surfaces divided into three distinct zones. The left and right zones 31 and 33, respectively, of the top surface of the strap are a generally smooth backing surface material. The left and right zones 32 and 34, respectively, of the bottom surface of the strap are of hook type VELCRO material adapted to attach to the loop type VELCRO material of base plate 20 with gentle pressure. The central portion 35 of the top surface of strap 30 is a high friction or tacky type material layer which is bonded or otherwise attached to the main strap portion. The central portion 36 of the bottom surface of strap presents a generally smooth surface similar to zones 31 and 33 of the top surface. This smooth surface could be formed by burning out or otherwise removing a band of the hooks from a continuous surface of VELCRO hook material. The reasons for arranging the various surfaces as just described will become more apparent from the following description of the use of the invention and with reference to FIGS. 3 and 4.

To use the TLC holder described, the following procedure will generally be used. First the adhesive side 21 of the base plate portion of the holder will be exposed by peeling away the covering 22. Then the base plate is placed upon the patient near the desired area of medical conduit support. Precise placement of the base plate isn't necessary due to the aforementioned adjustability. Next the medical conduit or conduits to be secured are wrapped in the strap portion of the holder. The strap is wrapped a full 360 degrees around the conduit in the following manner. The conduit is positioned atop the high friction portion of the strap at approximately a 90 degree angle to the long dimension of the strap. The narrow end of the strap is wrapped up around the conduit then back down through slot 37, then back under the conduit to again extend in its original direction and orientation. The direction of the wrap is clearly shown in FIG. 3. At this point pulling on the opposite ends of the strap will cause the narrow portion 38 of the strap to slide through slot 37 and securely cinch up the enclosed conduit.

Finally, while maintaining tension on the strap by pulling on its ends, the downwardly facing VELCRO hooks on both ends of the strap can be pressed upon the base plate to complete the attachment.

Note that when the strap is wrapped in this manner the most exposed upper surface is the original smooth central section 36 of the bottom seen in FIG. 6. The reason for making this section smooth was so when it was wrapped the strap would present this smooth surface to the environment thus eliminating unwanted snagging on other objects in the environment and accomplishing one of the major goals of the invention. Also note that when the strap is wrapped in this manner, the high friction or tacky central section of the top as seen in FIG. 5 is smoothly and tightly pressed against the conduit thus eliminating unwanted lengthwise slipping of the conduit and accomplishing another of the major goals of the invention. Additionally note that when the strap is wrapped in this manner, VELCRO fastening hooks 32 and 34 attach very near the side of the conduit nearest the patient's skin thus providing a connection with no play and accomplishing another major goal of the invention.

An additional feature of slot 37 is that it is formed of sufficient width in the axial direction of the strap so that a medical conduit of diameter approximately equal to this slot width standard sized section of surgical tubing may be passed through it. When this is done and the wrap cinched up as before, the extra conduit naturally aligns itself at approximately a 45 degree angle to the normally wrapped conduit but both conduits are firmly held in place by the strap. These variations are taught here in the expectation that the scope of patent protection, limited only by the appended claims, will include such variations.

It is to be understood that the provided illustrative examples are by no means exhaustive of the many possible uses for my invention. From the foregoing description, one skilled in the art can easily ascertain the essential characteristics of this invention and, without departing from the spirit and scope thereof, can make various changes and modifications of the invention to adapt it to various usages and conditions.

It is to be understood that the present invention is not limited to the sole embodiment described above, but encompasses any and all embodiments within the scope of the following claims.

We claim:

1. A conduit holder for releasably securing medical conduit to the external skin surface of a patient comprising:

base plate means having substantial area and comprising:
   a pliable support substrate easily contourable to a skin surface;
   a generally smooth upper attachment area; and
   a lower surface coated with medical grade adhesive for semi-permanent attachment to the skin of the patient;

strap means having a substantial length for looping around said conduit and adjustably but firmly securing said conduit generally parallel to the skin surface and orthogonal to said strap length; and pressure sensitive attachment means for holding said strap means to said upper attachment;

said strap means being fully detachable from said plate means, and having wide and narrow ends and a generally smooth transition zone between said ends; and said strap means further comprising:
   a generally smooth upper surface;
   a generally rough lower surface which, together with said generally smooth upper attachment area of said base plate means, forms said pressure sensitive attachment means; and
   a slot centrally located in said wide end near said transition zone, said slot having a width just sufficient to allow unimpeded passage of said narrow end through said slot and at the same time restraining said narrow end to remain axially aligned with said wide end after looping around said conduit;

said generally smooth upper surface of said strap means including a central band of high friction material for tightly gripping said conduit after looping around said conduit, said high friction band extending fully across the width of said strap and from approximately the region of said transition zone toward said narrow end of said strap means;

said generally rough lower surface of said strap means being interrupted by a relatively smooth central band for presenting a smooth exposed surface after looping around said conduit, said smooth central band extending fully across the width of said strap and from approximately the region of said transition zone toward said narrow end of said strap means.

2. The conduit holder according to claim 1, wherein said strap means is looped exactly 360 degrees around said conduit by passing under said conduit, up around said conduit, back down through said slot and back under said conduit.

3. The conduit holder according to claim 1, wherein said generally rough lower surface of said strap means is interrupted by a relatively smooth central band for presenting a smooth exposed surface after looping around said conduit, said smooth central band being located directly opposite said high friction band on said upper surface of said strap means.

4. The conduit holder according to claim 1, wherein said base plate means further comprises a sheet for covering said adhesive coating which is easily removed when it is desired to attach said base plate means to the skin of the patient.

5. The conduit holder according to claim 1, wherein said base plate means may be easily trimmed to fit awkward areas of the patient without compromising its effectiveness in providing secure attachment means for said medical conduit.

6. A conduit holder for releasably securing medical conduit to the external skin surface of a patient comprising:
base plate means comprising:
a pliable support surface easily contourable to a skin surface;
a generally smooth upper attachment area; and
a lower surface coated with medical grade adhesive for semi-permanent attachement to the skin of the patient; and
strap means having a substantial length for looping around said conduit and adjustably but firmly securing said conduit generally parallel to the skin surface and orthogonal to said strap length, said strap means being fully detachable from said plate means, and having wide and narrow ends and a generally smooth transition zone between said ends and comprising:
a generally smooth upper surface including a central band of high friction material for tightly gripping said conduit after looping around said conduit, said high friction band extending fully across the width of said strap and from approximately the region of said transition zone toward said narrow end of said strap means;
a generally rough lower surface which, together with said generally smooth upper attachment area of said base plate means, forms said pressure sensitive attachment means; and
a slot centrally located in said wide end near said transition zone, said slot having a width just sufficient to allow unimpeded passage of said narrow end through said slot and at the same time restraining said narrow end to remain axially aligned with said wide end after looping around said conduit; and
pressure sensitive attachment means for holding said strap means to said upper attachment area.

7. A conduit holder according to claim 6, wherein said base plate means has a substantial area so as to allow said pressure sensitive attachment means to hold said strap means to said upper attachment area in any direction throughout a full 360 degree range.

8. The conduit holder according to claim 6, wherein said strap means is looped exactly 360 degrees around said conduit by passing under said conduit, up around said conduit, back down through said slot and back under said conduit.

9. The conduit holder according to claim 6, wherein said base plate means further comprises a sheet for covering said adhesive coating which is easily removed when it is desired to attach said base plate means to the skin of the patient.

10. The conduit holder according to claim 6, wherein said base plate means may be easily trimmed to fit awkward areas of the patient without compromising its effectiveness in providing secure attachment means for said medical conduit.

11. A conduit holder for releasably securing medical conduit to the external skin surface of a patient comprising:
base plate means comprising:
a pliable support surface easily contourable to a skin surface;
a generally smooth upper attachment area; and
a lower surface coated with medical grade adhesive for semi-permanent attachement to the skin of the patient; and
strap means having a substantial length for looping around said conduit and adjustably but firmly securing said conduit generally parallel to the skin surface and orthogonal to said strap length, said strap means being fully detachable from said base plate means, and having wide and narrow ends and a generally smooth transition zone between said ends and comprising:
a generally smooth upper surface;
a generally rough lower surface which, together with said generally smooth upper attachment area of said base plate means, forms said pressure sensitive attachment means, wherein said generally rough lower surface of said strap means is interrupted by a relatively smooth central band for presenting a smooth non-tacky exposed surface after looping around said conduit, said smooth central band extending fully across the width of said strap and from approximately the region of said transition zone toward said narrow end of said strap means; and
a slot centrally located in said wide end near said transition zone, said slot having a width just sufficient to allow unimpeded passage of said narrow end through said slot and at the same time restraining said narrow end to remain axially aligned with said wide end after looping around said conduit; and
pressure sensitive attachment means for holding said strap means to said upper attachment area.

12. A conduit holder according to claim 11, wherein said base plate means has a substantial area so as to allow said pressure sensitive attachment means to hold said strap means to said upper attachment area in any direction throughout a full 360 degree range.

13. The conduit holder according to claim 11, wherein said strap means is looped exactly 360 degrees around said conduit by passing under said conduit, up around said conduit, back down through said slot and back under said conduit.

14. The conduit holder according to claim 11, wherein said base plate means further comprises a sheet for covering said adhesive coating which is easily removed when it is desired to attach said base plate means to the skin of the patient.

15. The conduit holder according to claim 11, wherein said base plate means may be easily trimmed to fit awkward areas of the patient without compromising its effectiveness in providing secure attachment means for said medical conduit.

* * * * *